United States Patent
Lindemer et al.

(10) Patent No.: US 11,282,196 B2
(45) Date of Patent: *Mar. 22, 2022

(54) AUTOMATED PATIENT COMPLEXITY CLASSIFICATION FOR ARTIFICIAL INTELLIGENCE TOOLS

(71) Applicant: International Business Machines Corporation, Armonk, NY (US)

(72) Inventors: Emily Lindemer, Allston, MA (US); David Richmond, Newton, MA (US); Marwan Sati, Mississauga (CA); Maria V. Sainz de Cea, Somerville, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/910,796

(22) Filed: Jun. 24, 2020

(65) Prior Publication Data

US 2020/0327668 A1 Oct. 15, 2020

Related U.S. Application Data

(63) Continuation of application No. 16/196,844, filed on Nov. 20, 2018, now Pat. No. 10,755,412.

(51) Int. Cl.
*G06T 7/00* (2017.01)
*G16H 30/40* (2018.01)
(Continued)

(52) U.S. Cl.
CPC .......... *G06T 7/0012* (2013.01); *G06K 9/6267* (2013.01); *G06N 3/08* (2013.01); *G16H 10/60* (2018.01); *G16H 30/40* (2018.01)

(58) Field of Classification Search
CPC .............................. G06N 20/00; G06T 7/0014
(Continued)

(56) References Cited

U.S. PATENT DOCUMENTS 9,600,628 B2 3/2017 Kisilev et al.
2002/0196965 A1 12/2002 Wallace et al.
(Continued)

FOREIGN PATENT DOCUMENTS

CN 106909778 A 6/2017

OTHER PUBLICATIONS

List of IBM Patents or Patent Applications Treated as Related, Jun. 24, 2020, 2 pages.

(Continued)

*Primary Examiner* — Kiet M Doan
(74) *Attorney, Agent, or Firm* — Stephen J. Walder, Jr.; Scott Dobson

(57) ABSTRACT

Mechanisms are provided for implementing a patient complexity classification (PCC) computing system. The PCC computing system receives medical image study data for a patient that comprises one or more medical image data structures and one or more corresponding medical image metadata data structures. A natural language processing engine of the PCC computing system performs natural language processing on the medical image metadata data structure to extract features indicative of at least one of patient or medical image characteristics. A complexity classifier of the PCC computing system evaluates the extracted features to determine a patient complexity indicating a complexity of a medical condition of the patient. Routing logic associated with the PCC computing system routes the one or more medical image data structures and one or more corresponding medical image metadata data structures to (Continued)

one or more downstream patient evaluation computing systems based on the determined patient complexity.

18 Claims, 4 Drawing Sheets

(51) Int. Cl.
  *G06K 9/62* (2022.01)
  *G06N 3/08* (2006.01)
  *G16H 10/60* (2018.01)
(58) Field of Classification Search
  USPC .............................................. 382/131; 705/3
  See application file for complete search history.

(56) References Cited

U.S. PATENT DOCUMENTS

| | | | |
|---|---|---|---|
| 2006/0095429 A1* | 5/2006 | Abhyankar | G16H 80/00 |
| 2011/0125734 A1 | 5/2011 | Duboue et al. | |
| 2013/0144652 A1* | 6/2013 | Roberson | G06F 19/00 705/3 |
| 2016/0066787 A1 | 3/2016 | Gluncic et al. | |
| 2018/0082487 A1 | 3/2018 | Kiraly et al. | |
| 2018/0114595 A1 | 4/2018 | Stern | |
| 2018/0166166 A1* | 6/2018 | Mabotuwana | G16H 15/00 |
| 2018/0242857 A1 | 8/2018 | Sharma et al. | |
| 2019/0392547 A1* | 12/2019 | Katouzian | G06N 3/0445 |
| 2020/0016051 A1 | 5/2020 | Lindemer et al. | |
| 2021/0174937 A1* | 6/2021 | Swisher | G06T 11/003 |

OTHER PUBLICATIONS

High, Rob, "The Era of Cognitive Systems: An Inside Look at IBM Watson and How it Works", IBM Corporation, Redbooks, Dec. 12, 2012, 16 pages.

Yuan, Michael J., "Watson and healthcare, How natural language processing and semantic search could revolutionize clinical decision support", IBM Corporation, IBM developerWorks, http://www.IBM.com/developerworks/industry/library/ind-watson/, Apr. 12, 2011, 14 pages.

* cited by examiner

AUTOMATED PATIENT COMPLEXITY CLASSIFICATION FOR ARTIFICIAL INTELLIGENCE TOOLS

BACKGROUND

The present application relates generally to an improved data processing apparatus and method and more specifically to an automated computer-implemented patient complexity classification (PCC) mechanism for artificial intelligence tools.

Decision-support systems exist in many different industries where human experts require assistance in retrieving and analyzing information. An example is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a patient complexity classification (PCC) computing system. The method comprises receiving, by the PCC computing system, medical image study data for a patient, wherein the medical image study data comprises one or more medical image data structures and one or more corresponding medical image metadata data structures. The method further comprises performing, by a natural language processing engine of the PCC computing system, natural language processing on the medical image metadata data structure to extract features indicative of at least one of patient or medical image characteristics. Moreover, the method comprises evaluating, by a complexity classifier of the PCC computing system, the extracted features to determine a patient complexity indicating a complexity of a medical condition of the patient. Furthermore, the method comprises routing, by routing logic associated with the PCC computing system, the one or more medical image data structures and one or more corresponding medical image metadata data structures to one or more downstream patient evaluation computing systems based on the determined patient complexity. Thus, in accordance with the illustrative embodiment, the complexity of the patient may be determined from the natural language processing of the medical image metadata quickly and efficiently so as to route the medical image study data to an appropriate downstream patient evaluation computing system without requiring integration with a patient electronic medical record (EMR) system or analysis of EMR data.

In other illustrative embodiments, the method further comprises performing, by one or more medical image analytics engines of the PCC computing system, image analytics on the medical image data structures to identify features, present in the medical images of the one or more medical image data structures, that are indicators of complexity (IOCs). Moreover, in these other illustrative embodiments, the method also comprises evaluating, by the complexity classifier of the PCC computing system, the IOCs to determine the level of complexity of the medical condition of the patient. Thus, with these illustrative embodiments, the complexity of the patient may be determined based on a combination of the natural language processing of the medical image study data metadata and the image data itself to thereby determine an appropriate downstream patient evaluation computing system to which to route the medical image study data.

In still other illustrative embodiments, the method further comprises determining, by the complexity classifier, whether or not the evaluation of the extracted features from the natural language processing of the medical image metadata data structure provides a complex patient classification, wherein the image analytics and evaluation of the IOCs are performed only in response to a determination that the evaluation of the extracted features from the natural language processing does not result in a complex patient classification. Thus, with these illustrative embodiments, if the patient is able to be determined to be complex based only on the natural language processing of the metadata, then the processing of the image data using analytics engines may be circumvented leading to a more rapid determination of complexity of the patient and routing of the medical image study data to an appropriate downstream patient evaluation computing system.

In some illustrative embodiments, the one or more medical image analytics engines are artificial intelligence computing engines configured and trained to perform computer vision analytic techniques on the one or more medical image data structures of the medical image study data to extract corresponding IOCs from the one or more medical image data structures. In some illustrative embodiments, the complexity classifier is a rules based computing engine that applies a plurality of predefined rules to the extracted features to determine which rules in the plurality of predefined rules have criteria that are satisfied by the extracted features, and wherein the patient complexity is determined based on which rules have criteria satisfied by the extracted features. In some illustrative embodiments, the complexity classifier comprises a configured and trained neural network that is trained using a supervised training operation to evaluate the extracted features from the medical image metadata data structure and the IOCs extracted from the medical image data, and to generate a patient complexity classification output. These artificial intelligence based engines lead to more accurate evaluation of the medical image study data for determining the complexity of the patient based on a learned basis for evaluation.

In some illustrative embodiments, the patient complexity classification output is one of a binary output indicating whether or not the patient is a complex patient or a non-complex patient, or a probability score indicating a probability of the patient being a complex patient or a non-complex patient. The binary output provides a clear indication of complexity or non-complexity of the patient which allows for a more streamlined and less complex logic for routing the medical image study data to an appropriate downstream patient evaluation computing system. With the probability score embodiments, a more fine grain evaluation of the complexity of the patient is achieved which allows for a more detailed routing of the medical image study data to downstream patient evaluation computing systems.

In some illustrative embodiments, the downstream patient evaluation computing systems comprise one or more artificial intelligence tools, wherein in response to the patient complexity indicating the patient to be complex, the medical study data is not routed to the one or more artificial intelligence tools and is routed to a human subject matter expert computing device for review and evaluation by the human subject matter expert. In these illustrative embodiments, if a patient is determined to be complex, the patient's medical image study data may be routed to a human subject matter expert that can provide a human evaluation of the complex medical image study data and make a determination as to the most appropriate treatment of the patient. Moreover, if the patient is not complex, then automated mechanism, such as the one or more artificial intelligence tools, may be used to perform a more rapid evaluation of the patient's medical image study data and identify appropriate treatment of the patient. In this way, the human subject matter expert's time and expertise are focused on the more complex patients while automated mechanisms may be used to assist with non-complex patients.

In some illustrative embodiment, the extracted features comprise at least one of an age of the patient, gender of the patient, a number of medical images present in the medical image study data, acquired image view position, or protocol name, and wherein the IOCs comprise at least one of abnormalities in the medical imaging data, presence of foreign bodies in the medical imaging data, or tissue density determinations. In still some illustrative embodiments, the medical image metadata data structure comprises Digital Imaging and Communications in Medicine header information.

In other illustrative embodiments, a computer program product comprising a computer useable or readable medium having a computer readable program is provided. The computer readable program, when executed on a data processing system, causes the data processing system to perform various ones of, and combinations of, the operations outlined above with regard to the method illustrative embodiments.

In yet another illustrative embodiment, a system/apparatus is provided. The system/apparatus may comprise one or more processors and one or more memories coupled to the one or more processors. The one or more memories may comprise instructions which, when executed by the one or more processors, cause the one or more processors to perform various ones of, and combinations of, the operations outlined above with regard to the method illustrative embodiments.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
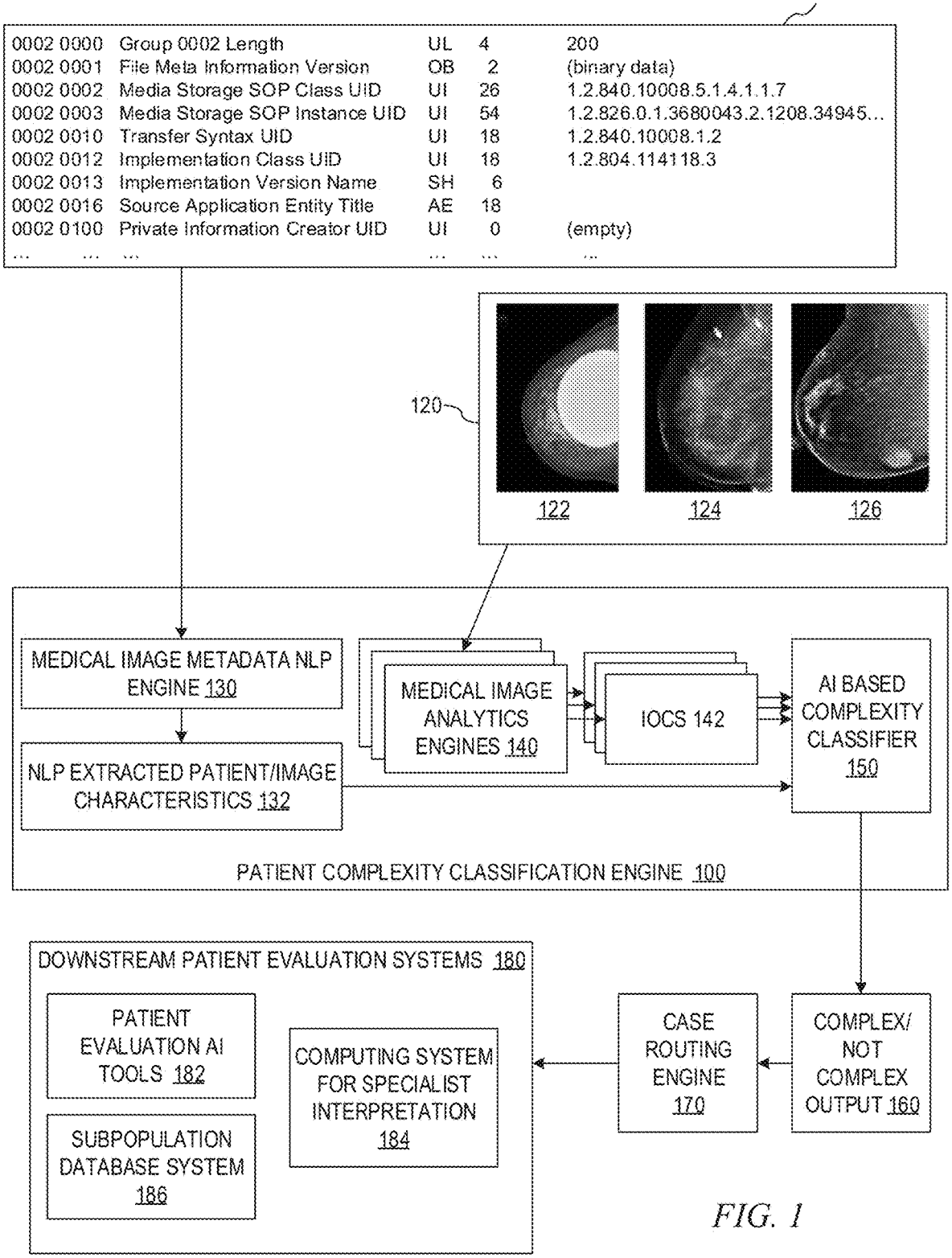
FIG. 1 is an example block diagram outlining an example workflow in accordance with one illustrative embodiment.

With the advent of artificial intelligence (AI) in healthcare, opportunities arise for the use of intelligent computing devices and machines in assessing patient information without human input or assistance. With these new opportunities, however, come new risks and challenges. These AI tools may employ neural networks, cognitive computing systems, or other AI mechanisms that are trained based on a finite set of data and can only be assuredly robust to assessing types of data that they have seen before. Thus, if one presents the AI tool with a set of information that is too novel or too complex to the AI tool, it will not be able to generate an accurate assessment, classification, treatment recommendation, or other output that the AI tool is configured to generate based on the input. In other words, the AI tool cannot generate accurate output if the input is too different from the training input used to train the AI tool. Thus, measures should be put in place to ensure that AI tools are not presented with these types of inputs that are too novel or complex as one cannot rely adequately on the output generated by the AI tool.

In the case of a healthcare medical imaging AI tool, there are many possible reasons why a patient's data may be considered to be too complex, or ineligible for AI processing by medical imaging AI tools that have been trained on a more "normal" patient population. Taking, as an example, a mammogram based medical imaging AI tool, these patients may have medical imaging data that indicates specialized situations, e.g., breast implants, particular types of tumors, or other breast conditions that may be out of the "normal" patient area, where "normal" refers to cases that are more often seen within the context, e.g., those types of patients that are more routine than out of the norm. These patients that are considered out of the norm may also need specialty follow-up or may be eligible to enter into separate databases for future studies of specific subpopulations. Identification of these complexities is a key aspect to being able to determine the best possible solution for evaluating and assisting the patient with their healthcare. While such identification may be able to be performed based on a detailed analysis of the patients' electronic medical records (EMRs), this requires integration with an EMR system and a potentially time consuming processing for evaluating a large number of factors that may be present in the EMR data, especially if one considers that EMR data may be formatted differently when it comes from a variety of different sources, medical personnel do not always represent medical data in a consistent manner, and other hurdles associated with such evaluation of EMR data.

The illustrative embodiments provide mechanisms for identifying patients with complexities in their medical conditions that would make them difficult to assess using downstream AI tools, based on medical imaging data alone. By relying only on the medical imaging data to make a determination as to whether the patient is considered too complex for AI tool evaluation, the evaluation of the patient is made more efficient than mechanisms that operate on EMR data. That is, using medical imaging data alone, the evaluation of the complexity of the patient may be performed more rapidly where EMR system integration is not available or is time consuming. Moreover, the medical imaging-based approach of the illustrative embodiments makes the complexity categorization of the illustrative embodiments more applicable in a generalized manner to many downstream use cases, as discussed hereafter.

In one or more illustrative embodiments, a patient is evaluated and categorized as to the patient's level of complexity based on a series of artificial intelligence (AI) filtering mechanisms that utilize both medical image metadata, e.g., Digital Imaging and Communications in Medicine (DICOM)® header information, and analysis of the digital medical image data itself (DICOM® is a registered trademark of the National Electrical Manufacturers Association (NEMA) for its standards publications relating to digital communications of medical information). The AI filtering mechanisms are agnostic as to the patient's electronic medical record (EMR) data and operate only on the medical imaging data and its associated metadata, which in the context of the examples set forth herein will be considered to be DICOM® header information, but in other illustrative embodiments may be any type of medical imaging data that may be presently available or later developed.

DICOM® is an international standard for transmitting, storing, retrieving, printing, processing, and displaying medical imaging information. The aims of the DICOM standard are to make medical imaging information interoperable and allow for integration of image-acquisition devices, PACs, workstations, VNAs and printers from different manufacturers. More information about DICOM® may be found at the DICOM® website at dicomstandard.org. As this is currently the predominant standard being used, it will be the standard for medical imaging metadata assumed to be associated with the medical imaging data in the examples set forth herein, however as noted above, the illustrative embodiments are not limited to such.

The illustrative embodiments implement a natural language processing (NLP) engine to operate on the DICOM® header information to extract features of the DICOM® header information that are indicative of the complexity of a patient's medical condition (hereafter referred to as the complexity of the patient). For example, in the medical area of mammography screening, the number of different tell-tale indicators that a patient is likely to be complex, i.e. have characteristics that make analysis by AI tools less accurate, include the types of images acquired during the medical imaging study, the number of medical images acquired, the patient's age, the patient's gender, the time elapsed since their previous medical imaging study, the presence of any foreign bodies in the medical image, and the tissue densities observed, among others. For some of these features, e.g., age, gender, number of medical images obtained, etc., natural language processing (NLP) performed on the DICOM® header information is sufficient to provide reliable classification of the patient as to whether they are complex or not complex.

However, in other cases, image-based artificial intelligence or deep learning analysis may also be needed to adequately classify the patient as to the patient's complexity and whether downstream AI tools may be used with sufficient accuracy to provide appropriate evaluation and healthcare assistance to the patient and/or medical personnel treating the patient. For example, such characteristics as the presence of foreign bodies in the medical images, tissue density, anomaly detection, and the like, DICOM® header information is not always reliable for representing this information such that NLP operations will not be able to extract such characteristics from the DICOM® header information. That is, the DICOM® header information relies on the radiologist or other medical imaging personnel to enter some of the information manually, e.g., presence of foreign bodies, tissue density measurements, etc., and human beings are not always reliable. Moreover, for some of this information, DICOM® may not have standards established for conveying such information such that the way in which this information is conveyed may differ from site to site.

Thus, in some illustrative embodiments, one or more image-based deep learning analytics or artificial intelligence mechanisms for performing deep learning analytics on the medical imaging data itself are provided to identify indicators of complexity (IOCs) in the medical imaging data. These IOCs may include the identification of specific abnormalities in the medical imaging data, the presence of foreign bodies in the medical imaging data (e.g., breast implants or other medical implants, biopsy clips, skin markers, etc.), tissue density determinations, and any other IOCs for which a deep learning analytics engine has been developed and trained.

Combinations of such IOCs may be obtained from the various trained deep learning analytics engines and provided to a patient complexity classifier engine along with the results of the NLP engine's analysis of the DICOM® header information. The patient complexity classifier engine may operate on the various inputs from these analysis engines using a trained artificial intelligence mechanism, e.g., a cognitive computing system, neural network, rules-based engine, or any combination of these elements, to generate a final determination as to whether the patient's medical condition is considered to be complex or not complex. Again, a medical condition considered to be complex is one that has characteristics indicative of the need for human intervention by a human subject matter expert, e.g., medical personnel or the like, and should not be forwarded to automated AI tools for evaluation. The trained artificial intelligence mechanisms of the patient complexity classifier engine evaluate the various inputs, using a weighted evaluation where the weights are learned through a supervised training process, through human subject matter expert specification (such as in the case of a rules based engine), or the like, such that various ones of the inputs may be weighted more highly than others depending on the determined criticality of those inputs to the complexity determination for the particular domain, e.g., mammography screening, pancreatic cancer screening, heart disease screening, or any other domain of interest to the particular implementation.

The particular combinations and weights applied to IOCs and/or NLP extracted characteristics of the patient from the DICOM® header information, may take many different forms depending on the particular implementation and the particular training of the AI mechanisms of the patient complexity classifier engine. Again, taking the mammography screening domain as an example, an abnormal number of medical images in a medical imaging study of a patient may be indicative that the radiologist found something suspicious in the medical images causing the radiologist to take additional images. This may be indicative of the fact that the patient is a complex patient. The fact that the patient is a male patient and is having a mammography screening may in itself be indicative of a complex patient case as males generally do not have mammography screenings. A patient having breast implants may be indicative of a more complex patient than patients that do not have such breast implants. A patient that comes in for their annual mammography screening may be less complex than a patient that has not come in for mammography screening previously, or has not come in for a mammography screening in more than a predetermined amount of time, e.g., within the last two years.

Each of these complexity factors, and other types of complexity factors, may be evaluated alone and in combination by the patient complexity classification (PCC) engine to thereby generate a final determination as to the classification of the patient as either complex or not complex. It should be appreciated that such a classification may be based on probability values or scores generated by the PCC engine from the evaluation of the various NLP characteristics and IOCs (collectively referred to as complexity factors herein), or may be a binary determination based on whether or not the complexity factors satisfy criteria specified in the PCC engine for classifying the patient as complex or not. For example, the PCC engine may implement a rules-based engine in which a rules database is provided that comprises a plurality of rules generated by subject matter experts (SMEs) for identifying patients that are complex. These rules may be executed by the computer logic of the rules-based engine on the complexity factors generated by the NLP and medical image data deep learning analytics engines (i.e. the characteristics and IOCs) to determine which rules have criteria that are satisfied by the complexity factors extracted from the medical image data and metadata associated with the medical image data, e.g., the DICOM® header information. A plurality of these rules may be applied to the complexity factors with each rule specifying a binary output as to whether or not the rule's criteria is satisfied or not. The combination of the outputs from the various rules may be used to generate a final binary output as to the complexity of the patient.

For example, in some implementations, if any rule indicates the patient to be complex, then the final output may indicate the patient to be complex. However, in other implementations, a predetermined threshold number of rules indicating the patient to be complex may be required in order to generate a final output indicating the patient to be complex. In still other implementations, a weighted evaluation of the rules may be implemented where weights may be associated with different rules such that the criteria of those rules are more or less important to the overall complexity determination relative to other rules in the rules database, e.g., gender may be less important than implant determinations in some implementations. The weighted value generated may be compared against a complexity threshold value such that if the complexity threshold value is met or exceeded, the patient may be classified as complex.

In embodiments in which a cognitive computing system or other artificial intelligence mechanism, such as a neural network, is trained to evaluate complexity factors when determining whether a patient is complex or not, the complexity factors generated by the NLP and medical image deep learning analytics engines may be fed as input into these artificial intelligence (AI) based mechanisms which are trained to weight the factors and combine them in a manner to generate a final classification output of complexity. The training of these AI mechanisms may involve a supervised training process in which a training dataset is input to the AI mechanisms which generate an output. The output is compared to a ground truth or otherwise evaluated by a human SME, which indicates the error, or loss, in the output. This error or loss is back propagated to the AI mechanism such that the weights of nodes or other operational parameters of the AI mechanism are modified to reduce the error or loss. This process is then repeated with the same or different training data in an iterative manner until the error or loss is within a tolerance, e.g., equal to or below a threshold amount of error or loss, at which time the AI mechanism is considered to have been trained or converged. The trained AI mechanism may then be applied to new inputs to thereby evaluate and classify those inputs with regard to complexity of the patient.

It should be appreciated that in some illustrative embodiments, a rules-based engine may be combined with AI mechanisms when implementing the PCC engine of the illustrative embodiments. For example, the rules-based engine may be used to generate outputs that are input to the AI mechanism for further evaluation. In some illustrative embodiments, the rules based engine may be used as an initial filter to identify clear cases of complex patients, while the AI mechanism may be employed as a second layer filter that evaluates patients whose complexity factors are less definitive of complexity, i.e. when the rules based engine does not indicate the patient to be complex or if the weighted complexity score generated from the output of the rules falls within a region of the threshold values indicating a potential for complexity but not definitive complexity. Any combination of rules-based engine and AI mechanisms may be used without departing from the spirit and scope of the present invention.

The complexity classification output generated by the PCC engine of the illustrative embodiments may be used to inform potential downstream AI processes as to whether they should evaluate the patient or if the patient's medical image data and other EMR data should be reviewed by a human SME or other medical personnel. It should be appreciated that the downstream AI tools to which the patient medical image data and EMR data may be input for evaluation may take many different forms and may have various use cases. The PCC engine may be used as an initial evaluation of the patient with regard to these various use cases by determining how complex the patient is and whether the patient is too complex for automated AI evaluation or not. For example, in one use case, the PCC engine may be used to determine the eligibility of the patient's medical imaging data for processing by another AI medical imaging tool. In some use cases, the PCC engine may be used to triage patients who require specialty reads, such as plastic surgery consults in the case of implants. Moreover, in other use cases, the PCC engine may be used to identify patients that may be candidates for subpopulations of complex patients on which to train new AI tools in order to enable future research and algorithm development. In such a case, the complex patients identified by the PCC engine may be flagged or their medical image data and/or EMR data provided to a subpopulation database for future use in training new AI tools.

In the case of triage, the PCC engine of the illustrative embodiments may be used to identify complex patients that need further evaluation by a specialist or follow-up care by a specialist. The PCC engine may automatically detect and notify the healthcare provider network about this need for follow-up without any human intervention, thereby reducing time and monetary expenditures. In the case of subpopulation candidates, the PCC engine of the illustrative embodiments makes possible the identification of complex medical imaging studies from a large medical imaging database, such as hospital database, for selective data harvesting and training of the AI tools on these specific complex patient subpopulations. In this way, the AI tools are trained to evaluate more complex populations than the previous AI tools that operate on a more normal range of patient medical conditions. These newly trained AI tools may be deployed to assist the other AI tools in the downstream processing discussed above, thereby leading to an ever-improving AI-based healthcare system.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for classifying patients as to the complexity of their medical conditions based on only the medical imaging data and its corresponding metadata, e.g., DICOM® header information. The illustrative embodiments may utilize natural language processing (NLP) operations to extract features from the natural language content of the metadata that identify characteristics of the patient and/or the medical images in the medical imaging study with which the metadata is associated. Logic is provided for determining whether the extracted features from the metadata are sufficient to make a determination as to the complexity of the patient's medical condition. Thereafter, in some illustrative embodiments, if the NLP feature extraction does not result in a complexity determination, or the patient is considered to be non-complex from the NLP feature extraction, a subsequent medical image data analysis is performed using medical image analytics engines employing artificial intelligence and computer vision techniques to identify indicators of complexity (IOCs) present in the medical image data itself. These IOCs are then evaluated by an AI-based complexity classifier along with the patient/image characteristics in the extracted features obtained from the NLP operation, to generate a determination as to whether the patient is considered complex or not complex. Based on the complexity determination, the patient's case may be routed to an appropriate downstream patient evaluation system for further processing or review by a human subject matter expert.

FIG. 1 is an example block diagram outlining an example workflow in accordance with one illustrative embodiment. As shown in FIG. 1, the patient complexity classification (PCC) engine 100 comprises a medical image metadata natural language processing (NLP) engine 130, one or more medical image analytics engines 140, and an AI-based complexity classifier 150. The PCC engine 100 generates a complexity output 160 indicating whether or not the patient being evaluated is considered to be a complex case or not. As noted above, the definition of a "complex" case is one where the likelihood is that downstream AI tool processing of the patient's medical data will result in poor performance, e.g., the AI tool has a high likelihood of generating an incorrect result. There may be many reasons as to why the AI tool may be determined to be inappropriate for processing a patient's medical data depending on the situation, and these reasons may be integrated into the training and evaluations of the complexity factors performed by the AI based complexity classifier 150 as discussed hereafter. For example, as noted above, if the downstream AI tool has been trained on "normal" patient data, which may include abnormalities that are generally seen in patient populations, the AI tool may be properly trained to operate on such normal patient data but may not be able to adequately and accurately evaluate patients that do not fall within the bounds of the "normal" range of patient data. Hence, these more "complex" patients should be flagged early on before being evaluated by the AI tools so as to avoid reliance on the AI tool outputs where these outputs may be inaccurate and potentially misleading.

With the PCC engine 100 a patient is evaluated and categorized as to the patient's level of complexity based on a series of artificial intelligence (AI) filtering mechanisms that utilize both medical image metadata, e.g., Digital Imaging and Communications in Medicine (DICOM)® header information, and analysis of the digital medical image data itself. The AI filtering mechanisms are agnostic as to the patient's electronic medical record (EMR) data and operate only on the medical imaging data and its associated metadata, e.g., DICOM® header information in the depicted examples.

The medical image metadata NLP engine 130, assuming an embodiment in which DICOM® header information is the metadata associated with the medical image data, implements a natural language processing (NLP) operation on the DICOM® header information to extract features of the DICOM® header information that are indicative of the complexity of the patient. The medical image metadata NLP engine 130 may be specifically configured with appropriate resources that are specific to the particular domain of patients or medical conditions being evaluated and is specifically configured to operate on the particular type of metadata, which in this case is DICOM® header information, in that domain. For example, the resources with which the medical image metadata NLP engine 130 is configured may comprise recognized medical codes, recognized terms, phrases, portions of text, dictionaries, synonym data structures, and the like, that are specific to the particular medical domain, e.g., mammography screening, heart disease, lung cancer, etc. In some embodiments, the medical image metadata NLP engine 130 may have a more general configuration to apply to a plurality of domains, but for purposes of illustration, it will be assumed that the medical image metadata NLP engine 130 is specifically configured for the particular domain of interest, which in the depicted examples is mammography screening.

The medical image metadata NLP engine 130 operates on the metadata 110 associated with the medical image data 120 to identify matching terms, phrases, portions of text, medical codes, etc. that may be present in the natural language content of the metadata 110. Natural language processing is generally known in the art and thus, a more detailed explanation of the specifics of natural language processing is not provided herein. In the present case, however, these NLP techniques are specifically configured and implemented for extracting features from the natural language content of medical image metadata 110, and in specific illustrative embodiments, DICOM® header information utilizing resources representing recognizable portions of the DICOM® standard that are of importance to the particular domain, e.g., mammography in the depicted example.

The medical image metadata NLP engine 130 generates the NLP extracted patient/image characteristics 132 from the medical image metadata 110. Examples of the NLP extracted patient/image characteristics 132 may include, for example, the age and gender of the patient, the number of medical images in the medical imaging study represented in the medical image data 120, acquired image view position, protocol name, etc. This information is useful in determining the complexity of the patient. For example, if the acquired image view position, e.g., MLO and CC being standard views for mammography screening, is a different view than would be expected for the particular medical imaging study, then this may be indicative of the patient being complex. Moreover, if the protocol name indicates "screening" or "implants study", and these protocol names are considered to be consistent for the particular reason for the medical imaging study, then this is informative that the patient may not be complex. Various individual or combinations of the NLP extracted patient/image characteristics 132 may be used to determine the complexity or non-complexity classification of the patient as discussed herein.

In some instances, the extracted patient/image characteristics from the medical image metadata may be sufficient to generate a determination as to the complexity of the patient with sufficient confidence. However, in other cases, this information alone may not be sufficient and an analysis of the medical imaging data itself may be necessary to obtain a more accurate determination as to the complexity of the patient. In such cases, the medical image analytics engines 140 are employed to perform computer vision operations and AI-based determinations of indicators of complexity (IOCs) 142 present in the medical image data itself, e.g., the presence of implants, the presence of biopsy clips, possible tumors or other abnormalities, etc. The IOCs and the extracted patient/image characteristics, together referred to as complexity factors, are then input to an AI-based complexity classifier 150 for evaluation and determination of a complexity classification of the patient 160.

As mentioned previously above, the number of different tell-tale indicators that a patient is likely to be complex in the area of mammography screening include the types of images acquired during the medical imaging study, the number of medical images acquired, the patient's age, the patient's gender, the time elapsed since their previous medical imaging study, the presence of any foreign bodies in the medical image, and the tissue densities observed, among others. For some of these features, e.g., age, gender, number of medical images obtained, etc., the natural language processing (NLP) performed by the medical image metadata NLP engine 130 on the medical image metadata 110 is sufficient to provide reliable classification of the patient as to whether they are complex or not complex. For example, if the patient is above the age of 50, the patient is male, or the medical imaging study contains more than an expected number of medical images, then this patient may be considered more complex than other patients.

However, in other cases, the medical image analytics engines 140 are employed to perform image based artificial intelligent or deep learning analysis to augment the metadata patient/image characteristic extraction to adequately classify the patient as to the patient's complexity and whether downstream AI tools may be used with sufficient accuracy to provide appropriate evaluation and healthcare assistance to the patient and/or medical personnel treating the patient. The medical image analytics engines 140 may employ computer vision analysis techniques to identify features present within the medical data indicative of various types of recognizable, and unrecognizable, anatomical structures. For example, the medical image analytics engines 140 may perform segmentation operations, extract contours, classify the contours as to the particular anatomical structures they represent, identify potential anomalies present in regions of the body, and the like. Each of the medical image analytics engines 140 may be specifically configured and trained to recognize different features within medical images.

The analytics engines 140 may be implemented as neural networks or other cognitive computing or artificial intelligence systems that are specifically configured and trained to identify particular types of anatomical structures, anomalies, etc. For example, one analytics engine 140 may be configured and trained to identify implants within a human breast. Another analytics engine 140 may be configured and trained to identify biopsy clips present in a human breast. Still another analytics engine may be configured and trained to identify anomalous tissue densities in a human breast that may be indicative of a tumor or growth. These identifications may be made based on the segmentation of the medical image, identification of contours associated with the various types of structures, and evaluation of these contours based on the training of the analytics engine 140. In some illustrative embodiments, the analytics engines 140 are trained using atlas images, i.e. training medical images which are labeled to identify various structures present in the medical images.

The analytics engines 140 extract features from the medical image data that may not otherwise be identified in the medical image metadata 110. These extracted features are collecting referred to as the IOCs 142. For example, features indicative of IOCs 142, such as the presence of foreign bodies in the medical images, tissue density, anomaly detection, and the like, are not always reliably identifiable from the DICOM® header information such that the NLP operations of the medical image metadata NLP engine 130 will not be able to extract such characteristics from the DICOM® header information. Thus, in some illustrative embodiments, the one or more image-based deep learning analytics or AI mechanisms of the analytics engines 140 are used to perform deep learning analytics on the medical imaging data 120 itself to identify the IOCs 142 in the medical imaging data 120. These IOCs 142 may include the identification of specific abnormalities in the medical imaging data, the presence of foreign bodies in the medical imaging data (e.g., breast implants or other medical implants, biopsy clips, skin markers, etc.), tissue density determinations, skin thickening, skin and scar markers, calcifications, and any other IOCs for which a deep learning analytics engine has been developed and trained.

In the example shown in FIG. 1, the medical image data 120 includes a plurality of individual medical images 122-126 represented as data structures that are obtained from one or more medical imaging computing systems (not shown). These medical imaging computer systems utilize medical imaging equipment that may implement various imaging technologies, such as x-ray imaging, magnetic resonance imaging (MRI), positron emission tomography (PET), computerized tomography (CT) imaging, or the like. In the depicted example, the images 122-126 are from different patients and are provided to illustrate examples of different types of structures that may be identifiable in medical image data. In an actual evaluation of a patient, all of the images would be from the same patient. Medical image 122 is provided as an example of a medical image of a human breast in which the patient has had a breast implant, represented as the large white region. Medical image 124 is provided as an example of a medical image of a human breast in which the patient has had a biopsy and biopsy clips are present, represented as the small bright white structures. Medical image 126 is provided as an example of a medical image of a human breast in which the patient has some anomalous structures represented by the areas of white in the image.

Combinations of such IOCs 142 may be obtained from the various trained deep learning analytics engines 140 and provided to a patient complexity classifier engine 150 along with the results of the medical image metadata NLP engine's 130 analysis of the medical image metadata 110, e.g., DICOM® header information. The patient complexity classifier engine 150 may operate on the various inputs from these analytics engines 140 using a trained artificial intelligence mechanism, e.g., a cognitive computing system, neural network, rules-based engine, or any combination of these elements, to generate a final determination 160 as to whether the patient's presentation is considered to be complex or not complex. The trained artificial intelligence mechanisms of the patient complexity classifier engine 150 evaluate the various inputs, using a weighted evaluation where the weights are learned through a supervised training process, through human subject matter expert specification, or the like, such that various ones of the inputs may be weighted more highly than others depending on the determined criticality of those inputs to the complexity determination for the particular domain, e.g., mammography screening in the depicted example.

The particular combinations and weights applied to IOCs 142 extracted from the medical image data 120 and/or NLP extracted characteristics of the patient/images 132 from the DICOM® header information 110, may take many different forms depending on the particular implementation and the particular training of the AI mechanisms of the patient complexity classifier engine 150. As mentioned above, in the mammography screening domain as an example, an abnormal number of medical images in a medical imaging study of a patient may be indicative that the radiologist found something suspicious in the medical images causing the radiologist to take additional images. This may be indicative of the fact that the patient is a complex patient. The fact that the patient is a male patient and is having a mammography screening may in itself be indicative of a complex patient case as males generally do not have mammography screenings. A patient having breast implants, such as in medical image 142, may be indicative of a more complex patient than patients that do not have such breast implants. A medical image showing biopsy clips, as in medical image 144, or abnormalities as in medical image 146, may be considered more complex than other patients. A patient that comes in for their annual mammography screening may be less complex than a patient that has not come in for mammography screening previously, or has not come in for a mammography screening in more than a predetermined amount of time, e.g., within the last two years.

Each of these complexity factors, and other types of complexity factors, may be evaluated alone and in combination by the patient complexity classifier engine 150 to thereby generate a final determination as to the classification of the patient as either complex or not complex. It should be appreciated that such a classification may be based on probability values or scores generated by the PCC engine 150 from the evaluation of the various NLP characteristics 132 and IOCs 142, i.e. the complexity factors, or may be a binary determination based on whether or not the complexity factors 132, 142 satisfy criteria specified in the patient complexity classifier engine 150 for classifying the patient as complex or not.

For example, the patient complexity classifier engine 150 may implement a rules-based engine in which a rules database is provided that comprises a plurality of rules generated by subject matter experts (SMEs) for identifying patients that are complex. The rules may specify one or more criteria for determining whether the rule should be "fired" or not, i.e. an indicator that the rule's criteria have been satisfied and a corresponding output generated. For example, a rule may specify that if the patient has not had their annual mammogram in more than a year, the patient is above a predetermined age, and the medical image study has more than X number of medical images present in the study, then the patient may be considered a complex patient. The rules may be composed such that the criteria may be based on patient/image characteristics 132 that are able to be extracted from the medical image metadata 110 alone, or a combination of the patient/image characteristics 132 from the medical image metadata 110 and IOCs 142 obtained from the analytics engines 140.

These rules may be executed by the computer logic of the rules-based engine in the AI-based complexity classifier engine 150 on the complexity factors generated by the medical image metadata NLP engine 130 and/or medical image data deep learning analytics engines 140 (i.e. the characteristics 132 and IOCs 142) to determine which rules have criteria that are satisfied by the complexity factors extracted from the medical image data 120 and metadata 110 associated with the medical image data 120, e.g., the DICOM® header information 110. In some illustrative embodiments, the rules may be rules that first operate on the characteristics 132 extracted from the metadata 110 to perform an initial determination as to whether the metadata alone provides sufficient characteristics to classify the patient as a complex patient. If the first subset of rules directed to the evaluation of the metadata 110 extracted characteristics 132, indicates that the patient cannot be classified as complex, then further evaluation by a second subset of rules directed to either the IOCs 142 from the medical image data 120 or a combination of the IOCs 142 and the metadata extracted characteristics 132, may be performed to determine if the patient is classified as complex or not. A plurality of these rules may be applied to the complexity factors 132 and/or 142 with each rule specifying a binary output as to whether or not the rule's criteria is satisfied or not. The combination of the outputs from the various rules may be used to generate a final binary output as to the complexity of the patient, i.e. an output 160 indicating that the patient is or is not complex.

For example, in some implementations, if any rule indicates the patient to be complex, then the final output 160 may indicate the patient to be complex. However, in other implementations, a predetermined threshold number of rules indicating the patient to be complex may be required in order to generate a final output 160 indicating the patient to be complex. In still other implementations, a weighted evaluation of the rules may be implemented where weights may be associated with different rules such that the criteria of those rules are more or less important to the overall complexity determination relative to other rules in the rules database, e.g., gender may be less important than implant determinations in some implementations. The weighted value generated may be compared against a complexity threshold value such that if the complexity threshold value is met or exceeded, the patient may be classified as complex in the final output 160.

It should be appreciated that in the above illustrative embodiments, a first subset of rules may be executed on the metadata extracted characteristics 132 and then a second subset of rules is executed if the first subset of rules does not indicate the patient to be complex. However, the illustrative embodiments are not limited to such. To the contrary, in some illustrative embodiments, the first and second subsets of rules may always be executed so that an evaluation of the combination of complexity factors 132, 142 is always performed.

It should be appreciated that the rules-based engine is only one possible implementation of the AI-based complexity classifier engine 150. In some illustrative embodiments, either in addition to, or alternative to, the rules-based engine, a cognitive computing system, neural network based system, or other artificial intelligence mechanism involving a machine learning system that is trained using training data and a supervised training process may be utilized to implement the AI based complexity classifier engine 150.

In embodiments in which a cognitive computing system or other artificial intelligence mechanism, such as a neural network, is trained to evaluate complexity factors when determining whether a patient is complex or not, the complexity factors generated by the medical image metadata NLP engine 130 and medical image deep learning analytics engines 140 may be fed as input into these artificial intelligence (AI) based mechanisms which are trained to weight the factors and combine them in a manner to generate a final classification output 160 of complexity. For example, the neural network of the AI based complexity classifier engine 150 may be trained by using a set of training data comprising patients medical image data and corresponding metadata for patients that are considered non-complex and others that are considered complex. The training data is input to the neural network which operates on the training data to generate an output classification as to whether the patient is considered complex or not, or a probability value associated with the classes of "complex" and "not complex". The correct output may be provided as a ground truth or a human SME may provide feedback indicating the correctness/incorrectness of the output generated by the neural network. The error may be fed back into the neural network by using training logic to modify the weights of nodes or changing other operational parameters of the neural network to modify its operation in order to reduce the error in the output of the neural network. This process may be repeated in an iterative fashion until the error or loss in the output of the neural network is reduced to an acceptable threshold indicating that the neural network is trained.

It should be appreciated that in some illustrative embodiments, a rules based engine may be combined with AI mechanisms when implementing the patient complexity classifier engine 150 of the illustrative embodiments. For example, the rules based engine may be used to generate outputs that are input to the AI mechanism for further evaluation. In some illustrative embodiments, the rules based engine may be used as an initial filter to identify clear cases of complex patients, while the AI mechanism may be employed as a second layer filter that evaluates patients whose complexity factors are less definitive of complexity, i.e. when the rules based engine does not indicate the patient to be complex or if the weighted complexity score generated from the output of the rules falls within a region of the threshold values indicating a potential for complexity but not definitive complexity. Any combination of rules based engine and AI mechanisms may be used without departing from the spirit and scope of the present invention.

The complexity classification output 160 generated by the patient complexity classifier engine 150 of the illustrative embodiments may be used to inform downstream patient evaluation systems 180 as to whether the patient is too complex for AI tools evaluation, whether the patient's medical image data and other EMR data should be reviewed by a human SME, whether the patient's medical image data and EMR data should be stored in a subpopulation for later training of AI tools or consideration for medical studies, or the like. In this way, the PCC engine 150 may be used as an initial evaluation of the patient with regard to various use cases by determining how complex the patient is and whether the patient is too complex for automated AI evaluation or not. The output 160 may be provided and used to drive case routing logic 170 which routes the patient's medical image data 120 (and corresponding metadata 110), as well as any patient EMR data that may be accessible, to an appropriate one of the downstream patient evaluation systems 180. For example, based on the classification of the patient as complex or not complex, the patient case (medical image data, metadata, and EMR data) may be routed to an AI tool 182, such as IBM Watson for Healthcare, available from International Business Machines Corporation, a workstation or other computing device 184 associated with a human SME for further review and evaluation based on the SME's expertise in the particular domain, or sent to a subpopulation database system 186 for storage and future consideration for training future AI tools and/or inclusion of the patient in other medical studies.

The PCC engine 100 may be used to provide complexity determinations of patients for a variety of different use cases. For example, in some illustrative embodiments, the PCC engine 100 provides a complexity output 160 for use in performing inclusion/exclusion determinations for medical studies. For example, companies may design AI tools that are intended to be used on specific populations of patients. For example, the Care Advisor for Breast (CAB) IBM Watson Health Imaging (WHI) product, available from International Business Machines Corporation, is intended to be used on patients that do not have prior surgeries, foreign bodies, or high breast density. As the CAB system and other similar products are used on patient data in real-time, automatic tools such as the PCC engine 100 of the illustrative embodiments assist the real-time operation by more quickly identifying which patients are able to be accurately evaluated by the CAB system and which require human intervention, thereby targeting the efforts of both the CAB system and the human SMEs on the patient data where their capabilities are best put to use.

In the case of a triage use case, the PCC engine 100 may be used to quickly identify, based on medical image data alone, complex patients that need further evaluation by a specialist or follow-up care by a specialist. The PCC engine 100 may automatically detect and notify the healthcare provider network about this need for follow-up without any human intervention, thereby reducing time and monetary expenditures.

In another use case, i.e. root cause analysis, the PCC engine 100 may be used to automatically determine which patient subpopulations and complexities are more challenging for the AI tools, i.e. result in a lower performance of the AI tools, to thereby inform subsequent development work and AI tool training. That is, in some embodiments, complex and non-complex patients may both be input to the AI tools and corresponding performance metrics may be collected to determine how well each AI tool operates on the complex and non-complex patients. In the case of complex patients, the reasons for the evaluation of the patient as being complex may be identified from the rules based engine and/or from the cognitive evaluation. This information may be used to identify subpopulations of complex patients and identify which types of complex patients the AI tools find difficult to process with sufficient performance.

In the use case of subpopulation candidate identification, the PCC engine 100 of the illustrative embodiments makes possible the identification of complex medical imaging studies from a large medical imaging database, such as hospital database, for selective data harvesting and training of the AI tools on these specific complex patient subpopulations. In this way, the AI tools are trained to evaluate more complex populations than the previous AI tools that operate on a more normal range of patient medical conditions. These newly trained AI tools may be deployed to assist the other AI tools in the downstream processing discussed above, thereby leading to an ever improving AI based healthcare system.

Thus, the illustrative embodiments provide automated specially configured computing mechanisms for classifying patients as to their complexity based only on the medical image metadata and medical image data. The illustrative embodiments extract patient and/or image study characteristics from the medical image metadata, which in some illustrative embodiments is DICOM header information, using natural language processing (NLP) techniques to extract features indicative of these characteristics. If needed, the illustrative embodiments may further perform medical image data analytics, using computer vision technologies, to identify features present in medical image data corresponding to indicators of complexity (IOCs). The IOCs and patient/medical image study characteristics (complexity factors) are evaluated using artificial intelligence based complexity classifier logic to determine a level of complexity of the patient, e.g., a binary output indicating the patient to be complex or not complex, a probability score indicating a probability that the patient is considered complex or not, or the like. This complexity output may be used to drive routing logic to route the patient's case to an appropriate downstream patient evaluation system. As a result, the patient's data is routed to the appropriate evaluation system for efficient and accurate evaluation of the patient's medical condition based on the complexity of the patient's medical condition as indicated by the patient's medical image data and corresponding medical image data metadata.

Figure 2:
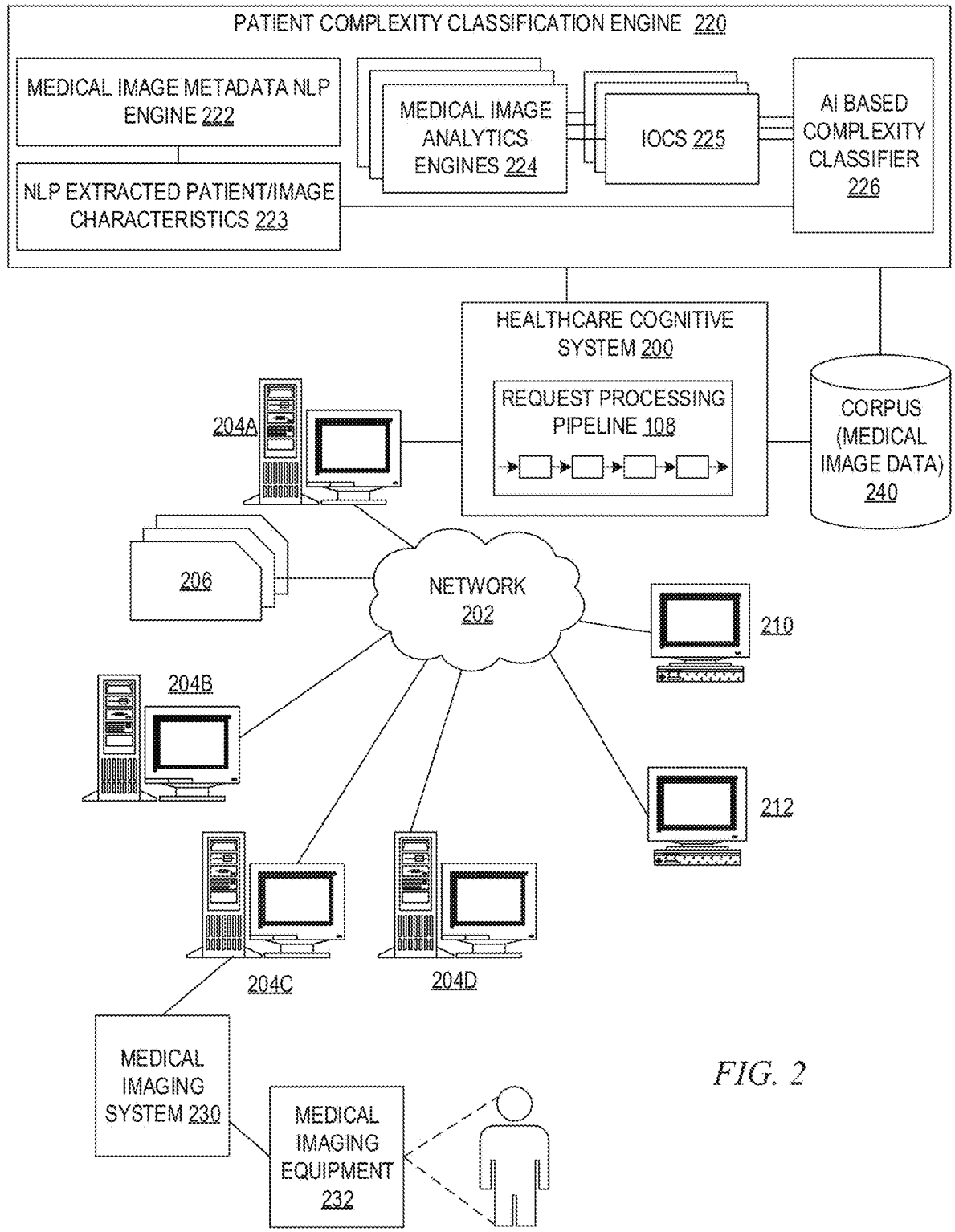
FIG. 2 depicts a schematic diagram of one illustrative embodiment of a cognitive healthcare system in a computer network in which aspects of a patient complexity classification (PCC) engine of the illustrative embodiments are implemented.
Figure 3:
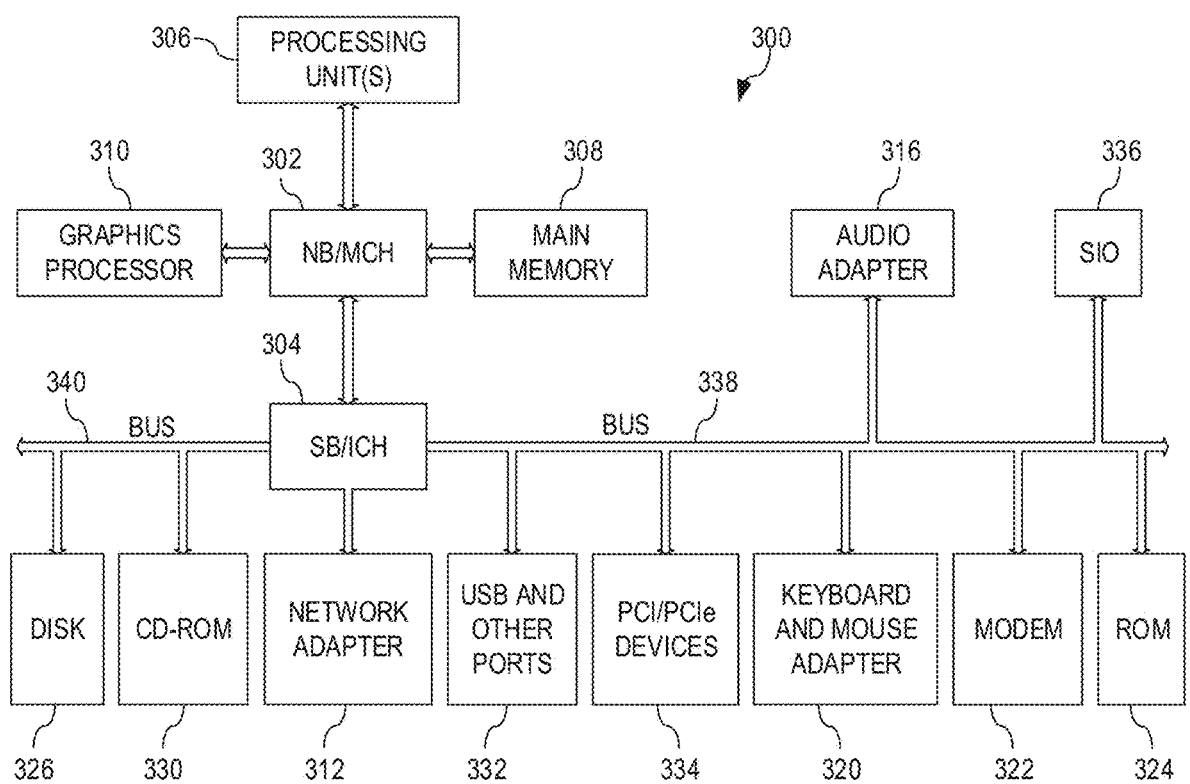
FIG. 3 is a block diagram of an example data processing system in which aspects of a PCC engine of the illustrative embodiments are implemented.

The illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

FIGS. 2-3 are directed to describing an example cognitive system for healthcare applications (also referred to herein as a "healthcare cognitive system") which implements a request processing pipeline, request processing methodology, and request processing computer program product with which the mechanisms of the illustrative embodiments are implemented. For example, the request processing pipeline may employ the PCC engine of the illustrative embodiments as an initial filtering mechanism for determining whether the pipeline should perform its cognitive evaluation of the patient medical image data, whether the patient's case should be routed to a workstation or computing device associated with a human SME for further evaluation, or the patient's case should be routed to a subpopulation database system for storage.

These requests that are input to the healthcare cognitive system, an example of which may be the IBM Watson™ Question Answering (QA) system, may be provided as structure or unstructured request messages, natural language questions, or any other suitable format for requesting an operation to be performed by the healthcare cognitive system. For example, the request may be a request to perform a cognitive operation on the patient medical image data, e.g., generate a treatment recommendation for the patient, evaluate the patient for a medical study, provide potential diagnoses for the patient, identify anomalies present in the patient medical image data, or the like. This request may, in some cases, be posed as a natural language question, e.g., "What treatment is suitable for patient X?", along with the input of the patient medical image data. Alternatively, the request may be a structured request asking for analysis of the patient medical image data.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of heart diseases) while another request processing pipeline may be trained to answer input requests in another medical malady domain (e.g., various types of lung cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for heart disease domain documents and another corpus for lung cancer diagnostics domain related documents in the above examples. In some cases, the request processing pipelines may each operate on the same domain of input questions but may have different configurations, e.g., different annotators or differently trained annotators, such that different analysis and potential results are generated. The healthcare cognitive system may provide additional logic for routing input requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

The healthcare cognitive system and request processing pipeline may be a downstream AI tool with which the mechanisms of the illustrative embodiments may be implemented. That is, the PCC engine of the illustrative embodiments may operate as an initial filter mechanism to identify complex patients and non-complex patients, where the complexity is determined relative to the particular cognitive operation being performed by the healthcare cognitive system and the domain of the healthcare cognitive system, as well as the training of the healthcare cognitive system. As such, the illustrative embodiments may be integrated in, augment, and extend the functionality of the request processing pipeline, or QA pipeline, mechanisms of a healthcare cognitive system with regard to identifying the complexity of patients based only on the patient's medical image data and corresponding metadata as an initial filter for identify which patients will be processed by the healthcare cognitive system with sufficient performance, and which will not. In cases where the patient is considered to be too complex for the healthcare cognitive system to process with sufficient performance, the patient's case may be forwarded to a human SME computer system, a subpopulation database system, or other appropriate computing system for further evaluation.

As the PCC engine of the illustrative embodiments may be utilized as an initial patient complexity filtering mechanism for a healthcare cognitive computing system, it is important to have an understanding of how cognitive computing systems and question and answer creation in a cognitive computing system implementing a request or QA pipeline is implemented. It should be appreciated that the mechanisms described in FIGS. 2-3 are only examples and are not intended to state or imply any limitation with regard to the type of cognitive system mechanisms with which the illustrative embodiments are implemented. Many modifications to the example cognitive system shown in FIGS. 2-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situational awareness that mimic human cognition based on experiences
- Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

The QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 2 depicts a schematic diagram of one illustrative embodiment of a cognitive system 200 implementing a request processing pipeline 208, which in some embodiments may be a question answering (QA) pipeline, in a computer network 202. For purposes of the present description, it will be assumed that the request processing pipeline 208 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the healthcare cognitive system 200 being implemented on computing device 204A only, but as noted above the healthcare cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like. In some illustrative embodiments, the healthcare cognitive system 200 and network 202 enables question processing and answer generation (QA) functionality for one or more cognitive system users via their respective computing devices 210-212. In other embodiments, the healthcare cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the healthcare cognitive system 200 may be used with components, systems, sub-systems, and/or devices other than those that are depicted herein.

The healthcare cognitive system 200 is configured to implement a request processing pipeline 208 that receive inputs from various sources. The requests may be posed in the form of a natural language question, natural language request for information, natural language request for the performance of a cognitive operation, or the like. For example, the healthcare cognitive system 200 receives input from the network 202, a corpus or corpora of electronic documents 206, cognitive system users, and/or other data and other possible sources of input. In one embodiment, some or all of the inputs to the healthcare cognitive system 200 are routed through the network 202. The various computing devices 204A-D on the network 202 include access points for content creators and cognitive system users. Some of the computing devices 204A-D include devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

In one embodiment, the content creator creates content in a document of the corpus or corpora of data 206 for use as part of a corpus of data with the healthcare cognitive system 200. The document includes any file, text, article, or source of data for use in the healthcare cognitive system 200. Cognitive system users access the healthcare cognitive system 200 via a network connection or an Internet connection to the network 202, and input questions/requests to the healthcare cognitive system 200 that are answered/processed based on the content in the corpus or corpora of data 206. In one embodiment, the questions/requests are formed using natural language. The cognitive system 200 parses and interprets the question/request via a pipeline 208, and provides a response to the cognitive system user, e.g., cognitive system user 210, containing one or more answers to the question posed, response to the request, results of processing the request, or the like. In some embodiments, the cognitive system 200 provides a response to users in a ranked list of candidate answers/responses while in other illustrative embodiments, the healthcare cognitive system 200 provides a single final answer/response or a combination of a final answer/response and ranked listing of other candidate answers/responses.

The healthcare cognitive system 200 implements the pipeline 208 which comprises a plurality of stages for processing an input question/request based on information obtained from the corpus or corpora of data 206. The pipeline 208 generates answers/responses for the input question or request based on the processing of the input question/request and the corpus or corpora of data 206.

In some illustrative embodiments, the healthcare cognitive system 200 may be the IBM Watson™ for Health Imaging (WHI) cognitive system available from International Business Machines Corporation of Armonk, N.Y., which is augmented with the mechanisms of the illustrative embodiments described herein as an initial filtering mechanism based on the complexity of the patient. As outlined previously, a pipeline of the IBM Watson™ cognitive system receives an input question or request which it then parses to extract the major features of the question/request, which in turn are then used to formulate queries that are applied to the corpus or corpora of data 206. Based on the application of the queries to the corpus or corpora of data 206, a set of hypotheses, or candidate answers/responses to the input question/request, are generated by looking across the corpus or corpora of data 206 for portions of the corpus or corpora of data 206 (hereafter referred to simply as the corpus 206) that have some potential for containing a valuable response to the input question/response (hereafter assumed to be an input question). The pipeline 208 of the IBM Watson™ cognitive system then performs deep analysis on the language of the input question and the language used in each of the portions of the corpus 206 found during the application of the queries using a variety of reasoning algorithms.

The scores obtained from the various reasoning algorithms are then weighted against a statistical model that summarizes a level of confidence that the pipeline 108 of the IBM Watson™ cognitive system 200, in this example, has regarding the evidence that the potential candidate answer is inferred by the question. This process is be repeated for each of the candidate answers to generate ranked listing of candidate answers which may then be presented to the user that submitted the input question, e.g., a user of client computing device 210, or from which a final answer is selected and presented to the user. More information about the pipeline 208 of the IBM Watson™ cognitive system 200 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 200 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, healthcare cognitive system 200 may provide a cognitive functionality for assisting with healthcare based operations. For example, depending upon the particular implementation, the healthcare based operations may comprise patient diagnostics, medical treatment recommendation systems, personal patient care plan generation and monitoring, patient electronic medical record (EMR) evaluation for various purposes, such as for identifying patients that are suitable for a medical trial or a particular type of medical treatment, or the like.

As shown in FIG. 2, the cognitive system 200 is further augmented, in accordance with the mechanisms of the illustrative embodiments, to include logic implemented in specialized hardware, software executed on hardware, or any combination of specialized hardware and software executed on hardware, for implementing a PCC engine 220 which may operate on the medical imaging data and corresponding metadata input to the healthcare cognitive system 200 to perform an initial complexity classification of the patient to determine whether further processing of the medical imaging data should be performed by the request processing pipeline 208 of the healthcare cognitive system 200.

As shown in FIG. 2, one or more of the server computing devices 204C may implement logic and processes for a medical imaging computing system 230 which may be used to generate medical image data for a patient. For example, a patient may have medical images of the patient's anatomy taken by medical imaging equipment 232 which are rendered as medical image data by a medical imaging computing system 230. A medical imaging specialist and/or automated process may generate medical image metadata that is appended to or otherwise linked to the medical image data via the medical imaging computing system 230. The resulting medical image data and corresponding medical image metadata may be provided to the healthcare cognitive system 200 where the medical image data/metadata is stored in a medical image data corpus 240 for processing in response to an input request. In response to an input request for processing of the medical image data/metadata, the healthcare cognitive system 200 may first cause the patient's complexity to be determined based on the medical image data/metadata alone to determine if further processing by the pipeline 208 should be performed, if the patient's case should be redirected to a SME workstation or other computing device for human review, or the patient's case should be maintained in a subpopulation database system for storage and future use.

The PCC engine 220 may operate on the medical image data/metadata in the manner previously described above with regard to FIG. 1 to determine a final classification of the patient as either complex or not complex. In making this determination, as described previously, the medical image metadata NLP engine 222 performs NLP operations to extract features indicative of patient/image study characteristics 223. The medical image analytics engines 224 perform cognitive or AI based analytics on the medical image data to extract indicators of complexity (IOCs) 225. These complexity factors 223 and 225 are input to the AI based complexity classifier 226 which may determine the final output indicating whether the patient is classified as complex or not. As noted previously, in some illustrative embodiments, a two stage filtering may be performed where the medical image analytics engines 224 are employed only in response to the medical image metadata NLP engine 222 extracted features 223 not providing a sufficient indication of the patient being complex. In other illustrative embodiments, both complexity factors 223 and 225 may always be evaluated by the AI based complexity classifier 226, which again may be implemented using a rules based engine, neural network, cognitive system, or other artificial intelligence system, or any combination of these artificial intelligence based mechanisms.

If the patient is determined to not be complex, the patient's medical image data may be input to the request processing pipeline 208 for further processing as it is determined that the patient is not too complex for a proper and accurate evaluation of the patient via the request processing pipeline 208. The request processing pipeline 208 may operate on the medical image data and other corpora data, e.g., from corpora 206 and the like, in order to perform a cognitive operation. If the patient is determined to be complex, the patient's case, including the medical image data and potentially the patient's EMR data, may be redirected to a human SME's computing system, such as client computing device 210, for further evaluation by the SME using their own domain specific expertise. Routing logic in the healthcare cognitive system 200 may be employed to take the complexity output generated by the AI based complexity classifier 226 and redirect the patient's medical image data to either the request processing pipeline 208 or the appropriate human SME's computing device 210. In some cases, the patient medical image data may be stored in a subpopulation database system for future use.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as servers 204A-D or client computing devices 210 and 212 in FIG. 2, in which computer usable code or instructions implementing the processes for illustrative embodiments of the present invention are located. In one illustrative embodiment, FIG. 3 represents a server computing device, such as a server 204A, which implements a healthcare cognitive system 200 and request processing pipeline 208 augmented to include the additional mechanisms of the illustrative embodiments with regard to the PCC engine 220.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p® computer system, running the Advanced Interactive Executive (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
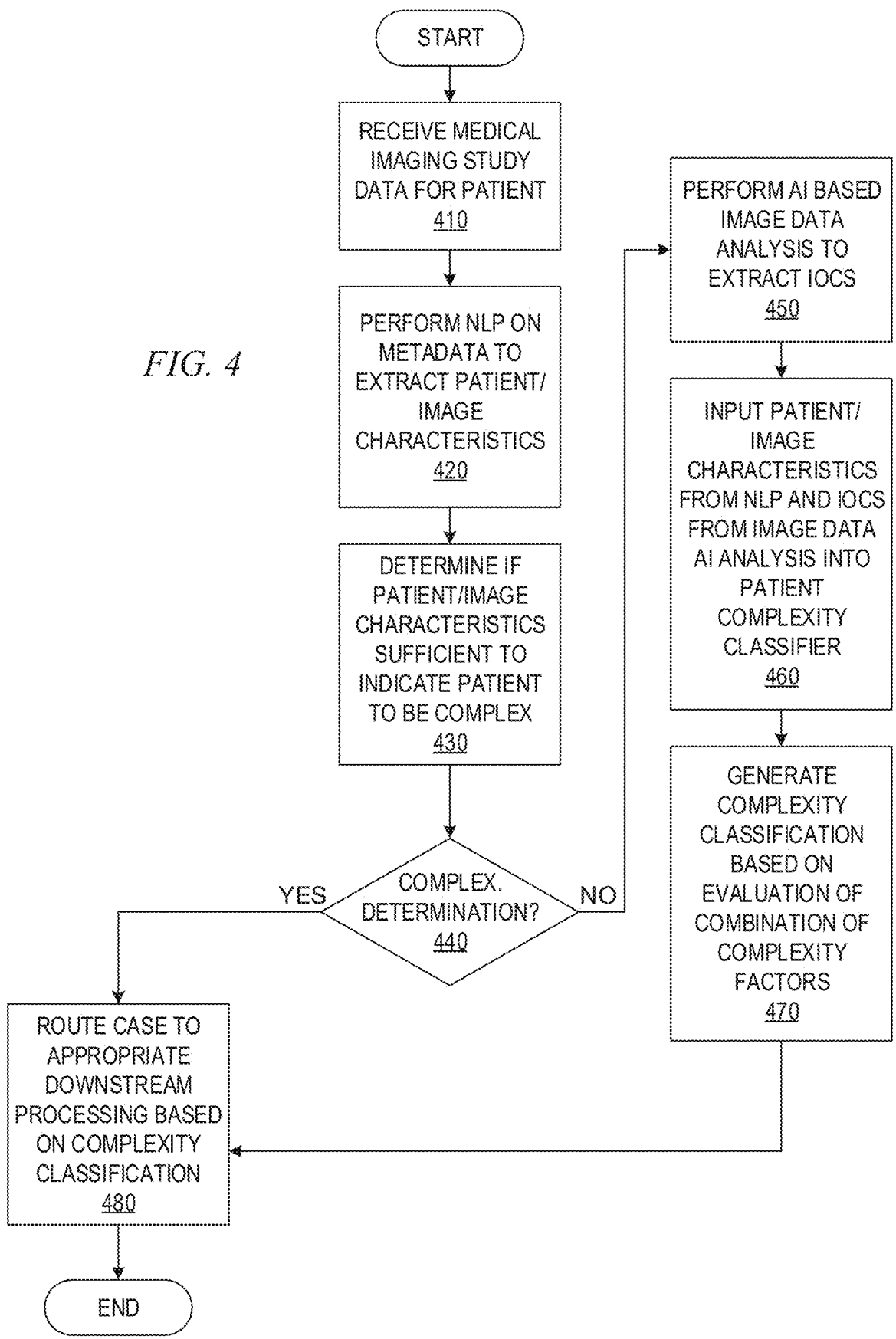
FIG. 4 is a flowchart outlining an example operation of a PCC engine in accordance with one illustrative embodiment.

FIG. 4 is a flowchart outlining an example operation of a patient complexity classification (PCC) engine in accordance with one illustrative embodiment. As shown in FIG. 4, the operation starts by receiving medical imaging study data for a patient (step 410). Natural language processing is performed on the metadata of the medical imaging study data to extract patient/medical image study characteristics (step 420). A determination is then made based on the extracted patient/medical image study characteristics to determine if there is sufficient information to classify the patient as complex (step 430). As noted above, this may involve a rules based engine evaluation, a neural network based evaluation, or other artificial intelligence based evaluation.

Based on the artificial intelligence evaluation of the extracted patient/medical image study characteristics a complexity determination is performed (step 440). If the complexity determination indicates a complex patient, the operation may proceed to step 480 as described hereafter. If the complexity determination is not able to identify the patient as complex, an AI based image data analysis is performed on the medical image data to extract indicators of complexity (IOCs) (step 450). The patient/medical image study characteristics from the NLP based extraction, and the IOCs identified from the AI based analytics performed on the medical image data are input to the patient complexity classifier (step 460). The patient complexity classifier generates a complexity classification based on an AI evaluation of the combination of these complexity factors (step 470). Based on the complexity classification from steps 440 or 470, the patient's case is routed to an appropriate downstream processing system (step 480) and the operation terminates. It should be appreciated that the downstream processing system may be a downstream AI tool, a human SME's computing system for human review and evaluation, a subpopulation database system for storage and future use, or the like.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a patient complexity classification (PCC) computing system, the method comprising:
   receiving, by the PCC computing system, medical image study data for a patient, wherein the medical image study data comprises one or more medical image data structures and one or more corresponding medical image metadata data structures;
   performing, by a natural language processing engine of the PCC computing system, natural language processing on the medical image metadata data structure to extract features indicative of at least one of patient or medical image characteristics;
   evaluating, by a complexity classifier of the PCC computing system, the extracted features to determine a patient complexity indicating a complexity of a medical condition of the patient; and
   routing, by routing logic associated with the PCC computing system, the one or more medical image data structures and one or more corresponding medical image metadata data structures to one or more downstream patient evaluation computing systems based on the determined patient complexity.

2. The method of claim 1, further comprising:
   performing, by one or more medical image analytics engines of the PCC computing system, image analytics on the medical image data structures to identify features, present in the medical images of the one or more medical image data structures, that are indicators of complexity (IOCs); and evaluating, by the complexity classifier of the PCC computing system, the IOCs to determine the level of complexity of the medical condition of the patient.

3. The method of claim 2, wherein the one or more medical image analytics engines are artificial intelligence computing engines configured and trained to perform computer vision analytic techniques on the one or more medical image data structures of the medical image study data to extract corresponding IOCs from the one or more medical image data structures.

4. The method of claim 2, wherein the complexity classifier comprises a configured and trained neural network that is trained using a supervised training operation to evaluate the extracted features from the medical image metadata data structure and the IOCs extracted from the medical image data, and to generate a patient complexity classification output.

5. The method of claim 4, wherein the patient complexity classification output is one of a binary output indicating whether or not the patient is a complex patient or a non-complex patient, or a probability score indicating a probability of the patient being a complex patient or a non-complex patient.

6. The method of claim 2, wherein the extracted features comprise at least one of an age of the patient, gender of the patient, a number of medical images present in the medical image study data, acquired image view position, or protocol name, and wherein the IOCs comprise at least one of abnormalities in the medical imaging data, presence of foreign bodies in the medical imaging data, or tissue density determinations.

7. The method of claim 1, wherein the complexity classifier is a rules based computing engine that applies a plurality of predefined rules to the extracted features to determine which rules in the plurality of predefined rules have criteria that are satisfied by the extracted features, and wherein the patient complexity is determined based on which rules have criteria satisfied by the extracted features.

8. The method of claim 1, wherein medical image metadata data structure comprises Digital Imaging and Communications in Medicine header information.

9. A method, in a data processing system comprising at least one processor and at least one memory, the at least one memory comprising instructions executed by the at least one processor to cause the at least one processor to implement a patient complexity classification (PCC) computing system, the method comprising:

receiving, by the PCC computing system, medical image study data for a patient, wherein the medical image study data comprises one or more medical image data structures and one or more corresponding medical image metadata data structures;

performing, by a natural language processing engine of the PCC computing system, natural language processing on the medical image metadata data structure to extract features indicative of at least one of patient or medical image characteristics;

evaluating, by a complexity classifier of the PCC computing system, the extracted features to determine a patient complexity indicating a complexity of a medical condition of the patient; and routing, by routing logic associated with the PCC computing system, the one or more medical image data structures and one or more corresponding medical image metadata data structures to one or more downstream patient evaluation computing systems based on the determined patient complexity, wherein the downstream patient evaluation computing systems comprise one or more artificial intelligence tools, and wherein in response to the patient complexity indicating the patient to be complex, the medical study data is not routed to the one or more artificial intelligence tools and is routed to a human subject matter expert computing device for review and evaluation by the human subject matter expert.

10. A computer program product comprising a computer readable storage medium having a computer readable program stored therein, wherein the computer readable program, when executed on a data processing system, causes the data processing system to implement a patient complexity classification (PCC) computing system that operates to:

receive medical image study data for a patient, wherein the medical image study data comprises one or more medical image data structures and one or more corresponding medical image metadata data structures;

perform, by a natural language processing engine of the PCC computing system, natural language processing on the medical image metadata data structure to extract features indicative of at least one of patient or medical image characteristics;

evaluate, by a complexity classifier of the PCC computing system, the extracted features to determine a patient complexity indicating a complexity of a medical condition of the patient; and route, by routing logic associated with the PCC computing system, the one or more medical image data structures and one or more corresponding medical image metadata data structures to one or more downstream patient evaluation computing systems based on the determined patient complexity.

11. The computer program product of claim 10, wherein the computer readable program further causes the PCC computing system to:

perform, by one or more medical image analytics engines of the PCC computing system, image analytics on the medical image data structures to identify features, present in the medical images of the one or more medical image data structures, that are indicators of complexity (IOCs); and evaluate, by the complexity classifier of the PCC computing system, the IOCs to determine the level of complexity of the medical condition of the patient.

12. The computer program product of claim 11, wherein the one or more medical image analytics engines are artificial intelligence computing engines configured and trained to perform computer vision analytic techniques on the one or more medical image data structures of the medical image study data to extract corresponding IOCs from the one or more medical image data structures.

13. The computer program product of claim 11, wherein the complexity classifier comprises a configured and trained neural network that is trained using a supervised training operation to evaluate the extracted features from the medical image metadata data structure and the IOCs extracted from the medical image data, and to generate a patient complexity classification output.

14. The computer program product of claim 13, wherein the patient complexity classification output is one of a binary output indicating whether or not the patient is a complex patient or a non-complex patient, or a probability score indicating a probability of the patient being a complex patient or a non-complex patient.

15. The computer program product of claim 11, wherein the extracted features comprise at least one of an age of the patient, gender of the patient, a number of medical images present in the medical image study data, acquired image view position, or protocol name, and wherein the IOCs comprise at least one of abnormalities in the medical imaging data, presence of foreign bodies in the medical imaging data, or tissue density determinations.

16. The computer program product of claim 10, wherein the complexity classifier is a rules based computing engine that applies a plurality of predefined rules to the extracted features to determine which rules in the plurality of predefined rules have criteria that are satisfied by the extracted features, and wherein the patient complexity is determined based on which rules have criteria satisfied by the extracted features.

17. A computer program product comprising a computer readable storage medium having a computer readable program stored therein, wherein the computer readable program, when executed on a data processing system, causes the data processing system to implement a patient complexity classification (PCC) computing system that operates to:
  receive medical image study data for a patient, wherein the medical image study data comprises one or more medical image data structures and one or more corresponding medical image metadata data structures;
  perform, by a natural language processing engine of the PCC computing system, natural language processing on the medical image metadata data structure to extract features indicative of at least one of patient or medical image characteristics;
  evaluate, by a complexity classifier of the PCC computing system, the extracted features to determine a patient complexity indicating a complexity of a medical condition of the patient; and
  route, by routing logic associated with the PCC computing system, the one or more medical image data structures and one or more corresponding medical image metadata data structures to one or more downstream patient evaluation computing systems based on the determined patient complexity, wherein the downstream patient evaluation computing systems comprise one or more artificial intelligence tools, and wherein in response to the patient complexity indicating the patient to be complex, the medical study data is not routed to the one or more artificial intelligence tools and is routed to a human subject matter expert computing device for review and evaluation by the human subject matter expert.

18. An apparatus comprising:
at least one processor; and
at least one memory coupled to the at least one processor, wherein the at least one memory comprises instructions which, when executed by the at least one processor, cause the at least one processor to implement a patient complexity classification (PCC) computing system that operates to:
receive medical image study data for a patient, wherein the medical image study data comprises one or more medical image data structures and one or more corresponding medical image metadata data structures;
perform, by a natural language processing engine of the PCC computing system, natural language processing on the medical image metadata data structure to extract features indicative of at least one of patient or medical image characteristics;
evaluate, by a complexity classifier of the PCC computing system, the extracted features to determine a patient complexity indicating a complexity of a medical condition of the patient; and
route, by routing logic associated with the PCC computing system, the one or more medical image data structures and one or more corresponding medical image metadata data structures to one or more downstream patient evaluation computing systems based on the determined patient complexity.

* * * * *